United States Patent [19]

Albert

[11] 4,149,076
[45] * Apr. 10, 1979

[54] METHOD AND APPARATUS PRODUCING PLURAL IMAGES OF DIFFERENT CONTRAST RANGE BY X-RAY SCANNING

[76] Inventor: Richard D. Albert, 317 Hartford Rd., Danville, Calif. 94526

[*] Notice: The portion of the term of this patent subsequent to Jun. 28, 1994, has been disclaimed.

[21] Appl. No.: 809,704

[22] Filed: Jun. 24, 1977

Related U.S. Application Data

[63] Continuation-in-part of Ser. No. 481,954, Jun. 24, 1974, Pat. No. 3,949,229.

[51] Int. Cl.² .............................................. G03D 41/16
[52] U.S. Cl. ............................... 250/402; 250/416 TV
[58] Field of Search ............ 250/416 R, 416 TV, 402, 250/401; 358/111

[56] References Cited

U.S. PATENT DOCUMENTS

| | | | |
|---|---|---|---|
| 3,582,651 | 6/1971 | Seedband | 250/416 TV |
| 3,852,605 | 12/1974 | Watanabe | 250/416 TV |
| 3,974,386 | 8/1976 | Mistretta | 250/416 TV |
| 4,032,787 | 6/1977 | Albert | 250/416 TV |

FOREIGN PATENT DOCUMENTS

| | | | |
|---|---|---|---|
| 2304427 | 8/1974 | Fed. Rep. of Germany | 250/416 TV |
| 2365510 | 4/1975 | Fed. Rep. of Germany | 250/416 TV |

*Primary Examiner*—Craig E. Church

*Attorney, Agent, or Firm*—Phillips, Moore, Weissenberger, Lempio & Majestic

[57] ABSTRACT

A plurality of radiographic images of a subject are obtained simultaneously by situating the subject between a scanning X-ray source and an X-ray detector. The source has an electron beam which is swept through a raster pattern on a broad target to produce a moving X-ray origin point while the detector has an effective radiation-sensitive area which is very small in relation to the raster pattern. The X-axis and Y-axis beam deflection signals which control the X-ray source are also transmitted to both sets of raster signal terminals of a dual-image oscilloscope of the form having two deflectable electron beams for producing two separate images at a display screen. Both intensity signal terminals of the oscilloscope receive processed X-ray count signals from the detector through separate signal channels so that a pair of radiographic images of the scanned region of the subject are generated at the display screen. Separate signal processing circuits in each channel may be adjusted to have different gain factors and to establish different base levels and peak levels for the intensity signals enabling each radiographic image to emphasize a different aspect of the scanned region of the subject as each image may have a different contrast range. The plural images taken in conjunction exhibit contrast ranges which may exceed the contrast limitations of a single oscilloscope image or the similar limitations of photographic film which may be used to record the oscilloscope display.

10 Claims, 1 Drawing Figure

U.S. Patent
Apr. 10, 1979
4,149,076
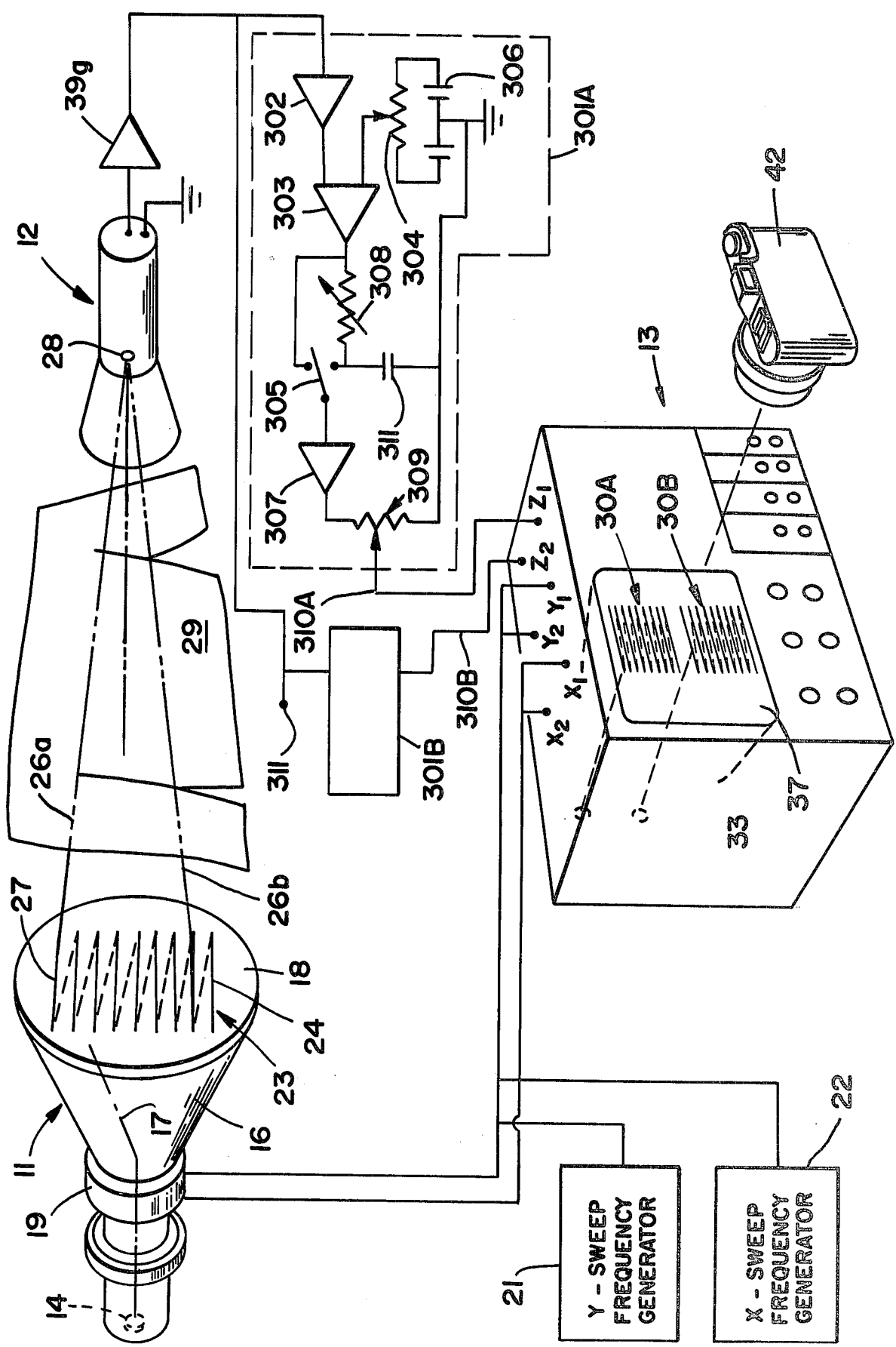

METHOD AND APPARATUS PRODUCING PLURAL IMAGES OF DIFFERENT CONTRAST RANGE BY X-RAY SCANNING

CROSS-REFERENCE TO RELATED APPLICATIONS

This application is a continuation-in-part of my copending application Ser. No. 673,908 filed Apr. 5, 1976 and entitled METHOD AND APPARATUS PRODUCING PLURAL IMAGES OF DIFFERENT CONTRAST RANGE BY X-RAY SCANNING, and which will issue June 28, 1977 as U.S. Pat. No. 4,032,787. Said application Ser. No. 673,908 is a continuation-in-part of application Ser. No. 481,954, filed June 24, 1974 and entitled X-RAY SCANNING METHOD AND APPARATUS and which is now U.S. Pat. No. 3,949,229.

BACKGROUND OF THE INVENTION

This invention relates to radiography and more particularly to a scanning X-ray system and method for simultaneously producing a plurality of radiographic images from a single scanning X-ray exposure of the subject in which the several images exhibit widely varying contrast-range characteristics to emphasize different aspects of the same region of the subject.

Conventional X-ray imaging systems in which the subject is situated between a fixed point X-ray source and a photographic film or fluorescent screen, are undesirably limited in the range of contrast obtainable in the image produced by a single exposure of the subject to X-rays. This has also been a characteristic of scanning X-ray systems in which the subject is situated between a point source of X-rays which sweeps through a raster pattern and an X-ray detector which controls light intensity at the screen of an oscilloscope undergoing a similar raster pattern to generate a single radiographic image at the screen of the oscilloscope. While oscilloscopes customarily have contrast and brightness controls, these must be set at some particular value during a single exposure of the subject. If these values are set to emphasize slight differences of X-ray absorbencies in the scanned area of the subject, such as differences between a tumor and healthy tissue in a medical patient, then other areas of widely differing X-ray absorbency such as bony structures and adjacent soft tissue are obscured in the image. If controls are set to contrast areas of the subject of widely different X-ray absorbency, then the areas of slight difference are obscured.

In general, most prior X-ray imaging systems are limited in their dynamic range of contrast to one or two orders of magnitude. Repeated exposures of the subject must be made to obtain desired information in many cases. In the case of the scanning system, as briefly described above, this does not result from any lack of information content in the signals produced by the X-ray detector in the course of a single scan of the subject, but instead derives from the limitations in the associated signal processing and display means, including the limited gray scale range of the oscilloscope screen and the limited contrast capabilities of photographic film which may be used to photograph the display on the oscilloscope screen.

SUMMARY OF THE PRESENT INVENTION

This invention alleviates the problem discussed above by providing for the simultaneous generation of a plurality of radiographic images of a given region of a subject, wherein each image may exhibit different contrast-range characteristics. This is accomplished by employing an X-Y display device, such as a cathode-ray tube oscilloscope or the like, of the form which has two or more sets of raster signal terminals and two or more electron beams for presenting two or more separate images at a single display screen. Each set of raster signal terminals receives the same X-axis and Y-axis deflection signals that control the scanning X-ray source. Thus, two or more spaced-apart moving points of light generation on the oscilloscope screen simultaneously sweep through raster patterns similar to that of the moving X-ray origin point at the X-ray source. The intensity of each point of light is controlled by the output of the X-ray detector, so that two or more separate radiographic images of the scanned region of the subject are produced at the screen.

To cause each image to exhibit a contrast range occupying a different portion of the full potential dynamic range of contrast contained in the X-ray detector output signals, an individual signal processing circuit is coupled between the detector and each intensity signal terminal of the multiple-image oscilloscope. Each such circuit may have a different gain factor which is preferably adjustable and each such circuit may provide for different intensity signal base levels and peak levels. In a preferred form, means are provided for selectively connecting a pulse integrating circuit into the X-ray count signal path to the associated oscilloscope, so that the system may be operated either on an individual X-ray count basis or on a detected X-ray flux level basis.

Accordingly, it is an object of this invention to provide for greater utilization of the information content generated in a scanning X-ray system.

It is another object of this invention to provide for the simultaneous production of plural images by a scanning X-ray system, wherein each image may exhibit different contrast ranges.

The invention, together with further objects and advantages thereof, will best be understood by reference to the following description of a preferred embodiment taken in conjunction with the accompanying drawing.

BRIEF DESCRIPTION OF THE DRAWING

The accompanying drawing is a diagrammatic view of a scanning X-ray system embodying the invention, wherein salient mechanical structures utilized in the system are shown in perspective form and electrical circuit elements are shown schematically.

DESCRIPTION OF A PREFERRED EMBODIMENT

My above-identified U.S. Pat. No. 3,949,229, issued Apr. 6, 1976, and entitled "X-RAY SCANNING METHOD AND APPARATUS", is hereby incorporated by reference and made a part of the present application.

Referring now to the accompanying drawing, component elements of a plural image scanning X-ray system may include a scanning X-ray source 11, an X-ray detector assembly 12 and at least one electronic image-producing means, which may be a cathode-ray tube oscilloscope 13 or other equivalent X-Y display device of the particular form which can simultaneously produce a plurality of separate images on a single screen.

The X-ray source 11 may be in part similar to a cathode-ray tube of the form having a cathode 14 at one end of an evacuated tube or envelope 16 from which electrons are accelerated in a beam 17 towards a broad anode or target plate 18 at the opposite larger end of the envelope. Beam deflection means such as a magnetic beam deflector coil assembly 19 is controlled by a Y-axis sweep frequency generator 21 and an X-axis sweep frequency generator 22 causing the electron beam 17 to scan the inner surface of target plate 18 in a raster pattern 23, in which the point of impact of the electron beam on the target plate is sequentially swept along a series of parallel spaced-apart, substantially linear scan lines 24. The scan lines 24 as depicted in the drawing are fewer in number and more widely spaced apart than is generally the case in practice in order to more clearly illustrate the method of operation. Target plate 18 of the X-ray source, is formed at least in part of a material, such as copper, silver or tungsten among many other examples, which emits X-rays 26 upon being bombarded by high-energy electrons. Thus, source 11, in effect, provides a moving point source of X-rays which may be systematically swept through the raster pattern 24.

The X-ray detector 12 may be of any of several known forms which produce output pulses indicative of individual X-ray counts or which produce an output signal indicative of the quantity of X-rays impinging on a radiation-sensitive area 28, the detector being a scintillation detector in this particular example. The effective radiation-sensitive area 28 of the detector should be substantially smaller than the area of the raster pattern 23 of the X-ray source 11. Preferably, the active sensitive area 28 of the detector should be as small as possible in relation to raster pattern 23, with due regard to obtaining an adequate response from the acceptable radiation flux level, as the difference in size of the sensitive area 28 and that of raster pattern 23, is a significant factor in determining definition in the radiographic images which are produced.

The X-ray detector 28 and the X-ray source 11 are spaced apart in order that a subject 29 to be examined may be situated between the source and detector in the path of X-ray radiation traveling from source target plate 18 towards the sensitive area 28 of the detector. In the present example, the subject 29 is the chest region of a medical patient; however, it should be understood that the invention is equally applicable to the production of radiographic images of other subjects, including inanimate objects, such as metallurgical castings, for example, which are to be examined for internal flaws.

The system may operate on either a pulse basis or on a continuous signal basis depending on the general level of the radiation flux transmitted through the subject and received by the detector 12. If the radiation flux level produced by the source 11 is kept sufficiently low that simultaneous receipt of a number of X-rays at detector 12 is infrequent, then the detector may be of the form producing a discrete output pulse for each individual detected X-ray. If the X-ray flux output of the source 11 is higher, so that there are normally a sizable number of X-rays being received at the detector 12, the detector may be of the form which produces a more or less continuous output signal having a voltage or current proportional to the instantaneous magnitude of detected X-ray radiation.

The image-producing display means 13 may be an X-Y display oscilloscope of the known dual-image or split-screen form for simultaneously displaying two separate images 30A and 30B. An oscilloscope of this kind may have a cathode-ray tube 33 with a large anode end defining a screen 37 which is formed in part of a phosphor material which emits visible light in response to bombardment by electrons. A pair of electron beams 35A and 35B are emitted towards screen 37 from two spaced-apart cathodes 36A and 36B, respectively, at the opposite end of the tube. A specific example of a dual-image oscilloscope suitable for the present purposes is the Model 7844 utilizing type 7A15A plug-in signal preamplifiers, which is manufactured and sold by Tektronix, Inc., Portland, Oreg., U.S.A. If permanent records of the images 30A and 30B which are produced at the screen 37 of the oscilloscope by the two electron beams 35A and 35B respectively are needed, a camera 42 may be disposed to view the screen 37 in order to photographically record the display on the screen.

Both X-axis or horizontal sweep signal terminals $X_1$ and $X_2$ of oscilloscope 13 for controlling the horizontal sweep motions of electron beams 35A and 35B, respectively, are coupled to the previously described X-sweep frequency generator 22 while both Y-axis or vertical sweep signal terminals $Y_1$ and $Y_2$ are coupled to the previously described Y-sweep frequency generator 21. Accordingly, electron beams 35A and 35B simultaneously undergo raster pattern scanning actions similar to that of the X-ray source 11 and concurrently with the scanning action of the source. Thus, at any given instant, the points of impact of the electron beams 35A and 35B at the associated image areas 30A and 30B, respectively, a phosphor screen 37 correspond with the point of impact of the electron beam 17 of the X-ray source on target plate 18 of the source. By utilizing the output signals of the X-ray detector 12 to modulate the intensity of the electron beams 35A and 35B of oscilloscope 13, two radiographic images of the scanned region of subject 29 are produced on the screen of the oscilloscope.

For this purpose, the output signals of detector 12 are initially amplified in a preamplifier 39g. An individual one of two signal processing circuits 301A and 301B is connected between the output of preamplifier 39g and each of the two separate electron beam intensity control signal terminal $Z_1$ and $Z_2$ of oscilloscope 13 for separately controlling the intensities of the electron beams 35A and 35B respectively. Each signal-processing circuit 301 may have a similar internal construction and accordingly only one such circuit, 301A, is depicted in detail in the drawing.

Each such signal-processing circuit such as circuit 301A may include an adjustable gain pulse shaping amplifier 302 which is connected between amplifier 39g and one input of a broad band differential D.C. coupled amplifier 303. To provide for selectively adjusting the base level of X-ray count signals, the reference input of amplifier 303 is coupled to the movable tap of a potentiometer 304 which has a resistive element connected across a bipolar D.C. power supply 306.

At one position of a mode selector switch 305, the output of amplifier 303 is connected directly to the input of a signal amplitude limiter amplifier 307. Amplifier 307 is operated near the saturation point to limit the maximum amplitude of the X-ray count signals to a predetermined level. The output of amplifier 307 is connected to circuit ground through the resistive element of a potentiometer 309 which has a movable tap connected through an output conductor 310A to the intensity control signal terminal $Z_1$ for electron beam 35A of the oscilloscope. The corresponding output conductor 310B of the other signal processing circuit 301B is similarly connected to the other intensity control signal terminal $Z_2$ for electron beam 35B of the oscilloscope.

Mode selector switch 305 has an alternate position at which output pulses generated by the X-ray detector are integrated to apply a varying voltage to the oscilloscope intensity terminal $Z_1$ which is indicative of detector output current rather than individual X-ray counts. At the alternate switch position, the direct connection between amplifiers 303 and 307 is opened and a similar connection is established through a variable resistor 308. To complete the integrating circuit, a capacitor 311 is connected between circuit ground and the circuit junction between resistor 308 and switch 305. By adjusting the resistor 308, the time constant of integration may be selected.

The alternate mode of operation is utilized when the X-ray count rate at detector 12 is sufficiently high that individual counts cannot be processed due to pulse pile-up.

Thus, the functions provided by each signal processing circuit 301A and 301B include establishing a predetermined selectable base level, by adjustment of potentiometer 304, for the signals applied to the associated one of the intensity terminals $Z_1$ and $Z_2$ of the oscilloscope 13. The maximum level of the signals applied to the associated oscilloscope intensity terminal Z is set by peak limiting amplifier 307 while adjustment of potentiometer 309 allows the gain factor of the signal-processing circuit to be selectively varied including providing for negative gain factors.

Since the output signal characteristics of each of the two signal-processing circuits 301A and 301B may be separately adjusted to provide different gains, different base levels and different peak levels for the intensity control signals applied to each of the two intensity control terminals $Z_1$ and $Z_2$, the two separate radiographic images produced at the screen 37 of the oscilloscope may be caused to exhibit different contrast characteristics to thereby emphasize different aspects of the scanned region of the subject 29.

The system as herein described for purposes of example produces two images of different contrast characteristics. The system may be extended to produce still more plural images of varying contrast ranges by providing one or more additional signal processing circuits 301 each controlling the intensity of a display at one or more additional oscillocopes which may be of either the single or multiple-image form. A terminal 311 for connecting such additional signal processing circuits to the output of preamplifier 39g may be provided to facilitate such usages of the invention.

While the invention has been disclosed with respect to a single representative embodiment, it will be apparent that many variations are possible and it is not intended to limit the invention except as defined in the following claims.

What is claimed is:

1. Apparatus for simultaneously producing plural radiographic images of a subject comprising:
    a scanning X-ray source having a broad target plate and an electron gun for directing an electron beam towards said target plate and having electron beam deflection means for sweeping said electron beam along said target plate in a first direction in response to a first sweep signal and a means for sweeping said electron beam in a second orthogonal direction in response to a second sweep signal to establish a moving origin point of X-rays on said target plate which sweeps through a raster pattern thereon,
    an X-ray detector spaced apart from said source whereby said subject may be disposed therebetween, said detector having an active radiation-sensitive area which is substantially smaller than said raster pattern and having means for producing X-ray count signals in response to X-rays which impinge on said radiation-sensitive area,
    at least one X-Y display device having a screen and means for producing a plurality of points of light at separate areas of said screen and having means for concurrently sweeping each of said points of light in a first direction in response to a first sweep signal and means for concurrently sweeping each of said points of light in a second orthogonal direction in response to a second sweep signal and having a plurality of signal terminals for receiving intensity signals to individually and concurrently control the intensities of each of said points of light,
    a first sweep frequency generator coupled to said x-ray source and to said display device to supply said first sweep signal thereto,
    a second sweep frequency generator coupled to said X-ray source and to said display device to supply said second sweep signal thereto, and
    a plurality of signal-processing circuits, each being connected to said X-ray detector and to an associated separate one of said intensity signal terminals to supply said intensity signals to said associated one of said intensity signal terminals, said signal-processing circuits having means for concurrently establishing a different predetermined intensity signal range for each of said intensity signal terminals in response to the same set of output signals from said detector.

2. The apparatus defined in claim 1 wherein each of said signal-processing circuits further comprises means for selectively varying the base level of the intensity signal applied to the associated one of said intensity signal terminals.

3. The apparatus defined in claim 1 wherein each of said signal-processing circuits has means for establishing a predetermined maximum amplitude for the intensity signals applied to the associated one of said intensity signal terminals.

4. The apparatus defined in claim 1 wherein each of said signal-processing circuits has a different amplification gain factor.

5. The apparatus defined in claim 4 further comprising means for individually adjusting said gain factor of each of said signal-processing circuits.

6. The apparatus defined in claim 1 wherein each of said signal-processing circuits has pulse-integrating means for converting a sequence of X-ray count pulses to a voltage having a magnitude indicative of the output current of said detector, and switch means for selectively connecting said integrating means into the signal path between said detector and the associated one of said intensity signal terminals.

7. The apparatus defined in claim 1 further comprising means for photographic said screen of said display device.

8. A method of simultaneously producing plural radiographic images of the subject wherein said images may exhibit different contrast-range characteristics, comprising the steps of:
  disposing said subject between a moving X-ray origin point and an X-ray detector,
  concurrently generating a plurality of points of light on a screen, each point of light being at a separate area thereof,
  synchronously sweeping said X-ray origin point and said points of light in similar raster patterns,
  modulating the intensity of a first of said points of light in response to variations of the output of said X-ray detector with an intensity signal which varies within a first range of signal amplitudes, and
  concurrently modulating the intensity of a second of said points of light in response to the same variations of the output of said X-ray detector with a second intensity signal which varies within a second different range of signal amplitudes.

9. The method defined in claim 8 further comprising the steps of modulating the intensity signal for a first of said points of light in accordance with a first gain factor and modulating the intensity signal for the second of said points of light in accordance with a second different gain factor.

10. The method defined in claim 9 further comprising establishing different base levels and different peak levels for said first and second intensity signals.

UNITED STATES PATENT OFFICE
CERTIFICATE OF CORRECTION

Patent No. 4,149,076  Dated  April 10, 1979

Inventor(s) Richard D. Albert

It is certified that error appears in the above-identified patent and that said Letters Patent are hereby corrected as shown below:

Col. 4, line 32    "a" should be --of--

Col. 6, line 67    "photographic" should be --photographing--

Signed and Sealed this

Ninth Day of October 1979

[SEAL]

Attest:

RUTH C. MASON
Attesting Officer

LUTRELLE F. PARKER
Acting Commissioner of Patents and Trademarks